(12) United States Patent
Wittland et al.

(10) Patent No.: US 7,404,278 B2
(45) Date of Patent: Jul. 29, 2008

(54) METHOD FOR PRODUCING PREFILLABLE SYRINGES

(75) Inventors: Frank Wittland, Enger (DE); Erik Brandhorst, Hiddenhausen (DE)

(73) Assignee: Gerresheimer Buende GmbH, Buende (DE)

( * ) Notice: Subject to any disclaimer, the term of this patent is extended or adjusted under 35 U.S.C. 154(b) by 0 days.

(21) Appl. No.: 11/706,787

(22) Filed: Feb. 14, 2007

(65) Prior Publication Data

US 2007/0186510 A1    Aug. 16, 2007

(30) Foreign Application Priority Data

Feb. 14, 2006   (EP) .................... 06002901

(51) Int. Cl.
  *B65B 55/24*   (2006.01)
(52) U.S. Cl. ................. 53/167; 53/127; 53/471
(58) Field of Classification Search .......... 53/167, 53/425, 426, 467, 471, 473, 475, 478; 422/28; 141/11
  See application file for complete search history.

(56) References Cited

U.S. PATENT DOCUMENTS

| 4,628,969 A | | 12/1986 | Juergens, Jr. et al. | |
| 4,718,463 A | * | 1/1988 | Jurgens et al. | 141/11 |
| 5,372,252 A | * | 12/1994 | Alexander | 422/25 |
| 5,597,530 A | * | 1/1997 | Smith et al. | 422/28 |
| 5,620,425 A | | 4/1997 | Heffernan et al. | |
| 5,687,542 A | * | 11/1997 | Lawecki et al. | 53/167 |
| 6,164,044 A | * | 12/2000 | Porfano et al. | 53/471 |
| 6,189,292 B1 | * | 2/2001 | Odell et al. | 53/425 |
| 6,250,052 B1 | * | 6/2001 | Porfano et al. | 53/471 |
| 6,263,641 B1 | | 7/2001 | Odell et al. | |
| 6,447,610 B1 | * | 9/2002 | Vetter | 118/215 |
| 6,792,743 B2 | * | 9/2004 | Odell et al. | 53/426 |
| 2006/0144705 A1 | * | 7/2006 | Hanstein | 204/415 |

\* cited by examiner

*Primary Examiner*—Louis K Huynh
(74) *Attorney, Agent, or Firm*—Laurence A. Greenberg; Werner H. Stemer; Ralph E. Locher

(57) ABSTRACT

A method for producing prefillable syringes includes the steps of producing syringe bodies with a cylindrical drum portion which has a first open end for receiving a syringe plunger and has a second open end for discharging of contents. An inner surface of each syringe body is then cleaned. Siliconization is then performed by applying a quantity of silicone oil or silicone emulsion to at least a partial area of the inner surface of each syringe body. Some of the applied quantity of silicone is then removed. Finally, the syringe bodies are packaged. The siliconization, removing and packaging steps are all carried out under controlled clean-room conditions.

19 Claims, 1 Drawing Sheet

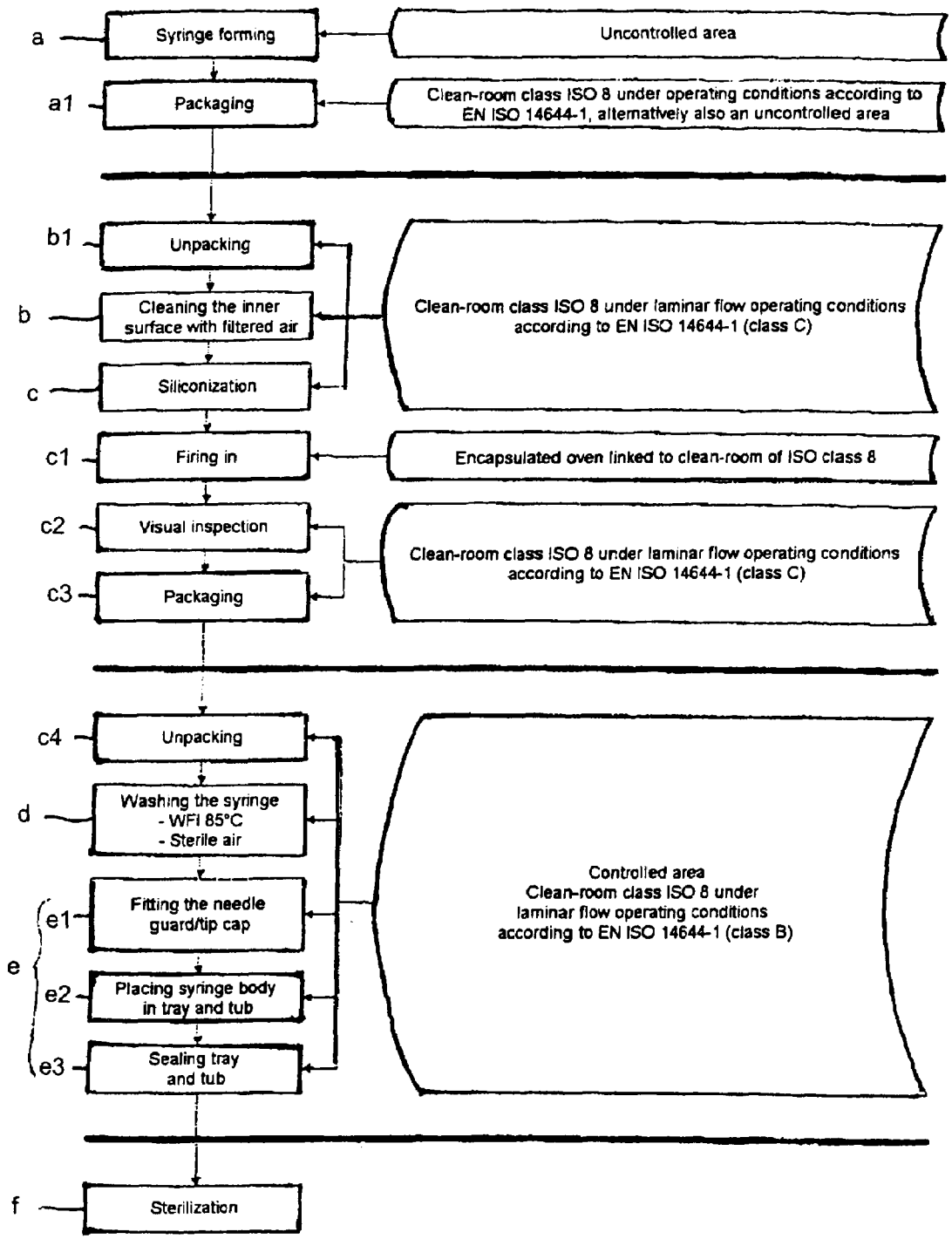

METHOD FOR PRODUCING PREFILLABLE SYRINGES

CROSS-REFERENCE TO RELATED APPLICATION

This application claims the priority, under 35 U.S.C. §119, of European application EP 06 002 901.4, filed Feb. 14, 2006; the prior application is herewith incorporated by reference in its entirety.

BACKGROUND OF THE INVENTION

Field of the Invention

The invention relates to a method for producing prefillable syringes. Syringe bodies are produced with a cylindrical drum portion which has a first open end for receiving a syringe plunger and has a second open end for discharging of contents. The inner surface of each syringe body is then cleaned and siliconization is achieved by applying a quantity of silicone oil or silicone emulsion to at least a partial area of the inner surface of each syringe body.

A method of this kind is known from U.S. Pat. No. 6,263,641 B1, for example, in which provision is also made that the syringe bodies are disposed in an array after siliconization and are packaged in a container. These can be syringe bodies made of plastic or glass.

When syringe bodies produced in this way are filled with a desired injectable medicament, some of the silicone oil, which in itself is medically safe and neutral, may interact adversely with the medicament and cause a deterioration in the effect of the latter. If the applied silicone oil or the silicone emulsion has been fired in during the production of the syringes, i.e. has been subjected to a temperature treatment of approximately 120° C. to 300° C. and more, some of the silicone is bonded covalently or by secondary valency to the glass surface of the syringe. However, an undesired crossover of the silicone into the medicament may occur as a result, for example, of the silicone oil being applied in excess quantities in some areas.

SUMMARY OF THE INVENTION

It is accordingly an object of the invention to provide a method for producing prefillable syringe that overcomes the above-mentioned disadvantages of the prior art methods of this general type, which, as far as possible the situation is avoided where the effect of a medicament introduced into the prefillable syringe is impaired due to interaction with insufficiently bonded silicone oil.

With the foregoing and other objects in view there is provided, in accordance with the invention, a method for producing prefillable syringes. The method includes the steps of:
a) producing syringe bodies having a cylindrical drum portion with a first open end formed therein for receiving a syringe plunger and a second open end formed therein for discharging of contents;
b) cleaning an inner surface of each of the syringe bodies;
c) performing a siliconization step by applying a quantity of silicone, selected from the group consisting of silicone oil and silicone emulsion, to at least a partial area of the inner surface of each of the syringe bodies;
c1) fixing the silicone applied on the syringe bodies by heat treatment at temperatures between 120° and 350° C.;
d) removing at least part of the silicone not covalently bonded or bonded by secondary valency; and
e) packaging the syringe bodies, and carrying out the steps c) through e) under controlled clean-room conditions.

According to the invention, the object is achieved, in a method of the type in question, by the steps of d) removing some of the applied quantity of silicone, and e) packaging the syringe bodies, with steps c) through e) being carried out under controlled clean-room conditions, in particular of ISO class 8, and under laminar flow operating conditions according to EN ISO 14644-1 (e.g. class B) or better. In the context of the invention, "controlled clean-room conditions" are understood as the continuous monitoring of air quality for maintaining fixed minimum standards, such as particle count or colony-forming units per cubic meter.

The invention preferably entails that, between steps c) and d), the applied silicone oil is fixed ("fired in") by heat treatment at temperatures of between 120° C. and 350° C. Provision can further be made that silicone that is not bonded or is not covalently bonded or bonded by secondary valency is completely or partially removed, for example 10% through 90% of the originally applied quantity, or 10% through 100% of the proportion of the original quantity that is not covalently bonded or bonded by secondary valency.

In particular, provision can be made that, in step d), a flushing operation is carried out with water or a solvent, for example alcohol. This can be done at a temperature in the range of 20° C. through 100° C., in particular 75° C. through 95° C., and preferably at 85° C. It is advantageous if the flushing operation is followed by drying with sterilized air.

Provision can further be made that, before step e), a needle guard or closure piece (a tip cap) is fitted.

In step e), a number of syringe bodies can be placed in a tray, the tray is inserted into a container, the latter closed with a cover and sealed, and the container packaged. Provision can be made for the packaged receptacle to be sterilized.

In one variant, provision can be made that the syringe bodies produced in step a) are packaged and, before step b), are unpacked under controlled clean-room conditions. In this connection, it is expedient that the syringe bodies are packaged and unpacked under clean-room conditions of ISO class 8 and under laminar flow operating conditions according to EN ISO 14644-1 or better.

The invention further provides that step e) is carried out under controlled clean-room conditions of ISO class 8 and under laminar flow operating conditions according to EN ISO 14644-1 or better.

If the siliconization is fired in, provision can be made for an encapsulated oven to be used which is linked to a clean-room area, e.g. of ISO class 8 or better.

In a further variant of the invention, provision can be made that syringe bodies produced in step c) are packaged and, before step d), are unpacked. Here too, it is possible for the syringe bodies to be packaged and unpacked under controlled clean-room conditions, in particular of ISO class 8 and under laminar flow operating conditions according to EN ISO 14644-1 or better.

In a preferred embodiment of the invention, provision is made that steps b) through e) are carried out under controlled clean-room conditions, in particular of ISO class 8, and under laminar flow operating conditions according to EN ISO 14644-1 or better.

Other features which are considered as characteristic for the invention are set forth in the appended claims.

Although the invention is illustrated and described herein as embodied in a method for producing prefillable syringes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

The single FIGURE of the drawing is a flow chart showing an example of a sequence of a method for producing prefillable syringes according to the invention.

DESCRIPTION OF THE PREFERRED EMBODIMENTS

Referring now to the single FIGURE of the drawing in detail, a method sequence is shown which illustrates the production of prefillable syringes right through to their being packaged in a form of an array of syringes in a closed and sterilized container (tub).

Step a concerns the production of a syringe body as such directly from forming of plastic or glass by a suitable device which is known per se and is not described in detail. In step a, syringe bodies are produced with a cylindrical drum portion which has a first open end for receiving a syringe plunger and has an opposite, second open end of smaller cross section for a discharging of contents. An injection needle is secured on the second open end at a suitable stage of the method described here, or not until immediately before the use of the fillable or already filled syringe. For this purpose, various techniques are employed which are known per se and are not described in detail here, for example gluing, mounting or locking.

In step a1, the syringe bodies that have been produced in this way are packaged. The packaging operation can be carried out under controlled clean-room conditions, in this case of ISO class 8, and under operating conditions according to EN ISO 14644-1. Alternatively, the syringe bodies are produced and also packaged in a production area in which the degree of cleanliness is not controlled.

In step b1, the syringe bodies that have been packaged as described above are unpacked under controlled clean-room conditions, in this case of ISO class 8, and under laminar flow operating conditions according to EN ISO 14644-1 (e.g. class C).

In a further step b, the inner surface of the syringe body is cleaned, for example with cleaned or sterile air, or with ionized air, likewise under controlled conditions as in step b1.

In step c, the inner surface of the syringe body is siliconized under controlled conditions as in steps b1 and b, with silicone oil or a silicone emulsion being suitably applied to the inner surface, for example sprayed onto it. In this connection, a predetermined quantity of silicone can be applied. Provision can additionally be made for excess silicone to be immediately removed, for example by wiping or flushing it off.

In step c1, provision is preferably made for the applied silicone oil to be fixed in a suitable manner, in this example by a temperature treatment at least approximately 120° C. (autoclaving) up to 350° C. (firing in) for a prescribed duration of treatment. For the temperature treatment, an encapsulated oven is used which is linked to a clean-room area, in particular to an area with ISO cleanliness class 8.

Step c2 involves a visual inspection of the syringe bodies under clean-room operating conditions, in particular as in steps b1 through c, and step c3 involves packaging the syringe bodies under corresponding conditions.

Step c4 involves unpacking the syringe bodies packaged in step c3, and these syringe bodies, in step d, are then, flushed through in the prescribed manner with WFI (water for injection, flushing water with a prescribed purity specification), for example at a temperature of 85° C. They are then dried with sterile air.

In step e1, the syringe bodies are provided with further parts, depending on the type of syringes to be manufactured, for example with a needle guard, a closure piece (tip cap) and/or other parts.

Step e2 involves arranging a group of syringe bodies in a tray which is placed in a container (tub) which is in turn then closed once a cover has been applied (step e3).

In step f, the syringe bodies located in the packaging, and the packaging itself, are sterilized, in particular with gas, for example ethylene oxide (ETO). This step can be carried out remote from and independently of the preceding steps.

In the example shown, all of method steps c4 through e3 take place under controlled clean-room conditions, in this case under conditions of ISO class 8 and under laminar flow operating conditions according to EN ISO 14644-1 (e.g. class B), or better.

As is indicated in the figure by the bolded horizontal dividing lines, the otherwise continuous method sequence can be interrupted between steps a1 and b1 and/or between steps c3 and c4 and/or between steps e3 and f, by the packaged syringe bodies being intermediately stored, for example, and then being delivered as and when required to the respective unpacking step b1 or c4 or sterilization step f. Alternatively, the packing and unpacking steps can be omitted and the production method can be carried out completely continuously, and at all times under clean-room conditions.

We claim:

1. A method for producing prefillable syringes, which comprises the steps of:
   a) producing syringe bodies having a cylindrical drum portion with a first open end formed therein for receiving a syringe plunger and a second open end formed therein for discharging of contents;
   b) cleaning an inner surface of each of the syringe bodies;
   c) performing a siliconization step by applying a quantity of silicone, selected from the group consisting of silicone oil and silicone emulsion, to at least a partial area of the inner surface of each of the syringe bodies;
   c1) fixing the silicone applied on the syringe bodies by heat treatment at temperatures between 120° and 350° C.;
   d) removing at least part of the silicone not covalently bonded or bonded by secondary valency; and
   e) packaging the syringe bodies, and carrying out the steps c) through e) under controlled clean-room conditions.

2. The method according to claim 1, which further comprises carrying out the steps c) through e) continuously under clean-room conditions of ISO class 8 and under laminar flow operating conditions according to EN ISO 14644-1 or better.

3. The method according to claim 1, which further comprises during the step d), carrying out a flushing operation with one of water and a solvent.

4. The method according to claim 3, which further comprises carrying out the flushing operation at a temperature in a range of 20° C. to 120° C.

5. The method according to claim 3, which further comprises following the flushing operation, performing a drying step with sterile air.

6. The method according to claim 3, which further comprises carrying out the flushing operation at a temperature in a range of 75° C. to 95° C.

7. The method according to claim 1, which further comprises before performing the step e), fitting one of a needle guard and a closure piece to each of the syringe bodies.

8. The method according to claim 1, which further comprises during the step e):
placing a number of the syringe bodies in a tray;
inserting the tray into a container;
closing the container with a cover for sealing the container; and
packaging the container.

9. The method according to claim 1, which further comprises packaging the syringe bodies produced in the step a) and, before performing the step b), unpacking the syringe bodies under the controlled clean-room conditions.

10. The method according to claim 9, which further comprises performing the packaging and the unpacking steps of the syringe bodies under clean-room conditions of ISO class 8 and under laminar flow operating conditions according to EN ISO 14644-1 or better.

11. The method according to claim 1, which further comprises carrying out the step e) under clean-room conditions of ISO class 8 and under laminar flow operating conditions according to EN ISO 14644-1 or better.

12. The method according to claim 1, which further comprises using an encapsulated oven linked to a clean-room area of ISO class 8 or better for performing the heat treatment step.

13. The method according to claim 1, which further comprises:
packaging the syringe bodies produced in the step c); and
unpacking the syringe bodies before performing the step d).

14. The method according to claim 13, which further comprises performing the packaging step and the unpacking step under the controlled clean-room conditions.

15. The method according to claim 14, which further comprises performing the packaging step and the unpacking step under the controlled clean-room conditions of ISO class 8 and under laminar flow operating conditions according to EN ISO 14644-1 or better.

16. The method according to claim 1, which further comprises carrying out the steps b) through e) under the controlled clean-room conditions.

17. The method according to claim 16, which further comprises carrying out the steps b) through e) under the clean-room conditions of ISO class 8 and under laminar flow operating conditions according to EN ISO 14644-1 or better.

18. The method according to claim 1, which further comprises during the step d), carrying out a flushing operation with one of water and alcohol.

19. The method according to claim 1, which further comprises before performing the step e), fitting one of a needle guard and a tip cap to each of the syringe bodies.

* * * * *